US012749581B2

(12) United States Patent
Ding et al.

(10) Patent No.: US 12,749,581 B2
(45) Date of Patent: Sep. 29, 2026

(54) DEPTH NETWORK DETECTION METHOD FOR DIABETIC RETINOPATHY BASED ON GENETIC FUZZY TREE

(71) Applicant: NANTONG UNIVERSITY, Jiangsu (CN)

(72) Inventors: Weiping Ding, Jiangsu (CN); Haipeng Wang, Jiangsu (CN); Hengrong Ju, Jiangsu (CN); Chuansheng Liu, Jiangsu (CN); Yu Geng, Jiangsu (CN); Jiashuang Huang, Jiangsu (CN); Chun Cheng, Jiangsu (CN); Jinxin Cao, Jiangsu (CN); Tingzhen Qin, Jiangsu (CN); Xinjie Shen, Jiangsu (CN); Bairu Pan, Jiangsu (CN)

(73) Assignee: NANTONG UNIVERSITY, Jiangsu (CN)

( * ) Notice: Subject to any disclaimer, the term of this patent is extended or adjusted under 35 U.S.C. 154(b) by 257 days.

(21) Appl. No.: 18/258,511

(22) PCT Filed: Feb. 23, 2023

(86) PCT No.: PCT/CN2023/077768
§ 371 (c)(1),
(2) Date: Sep. 26, 2024

(87) PCT Pub. No.: WO2023/143628
PCT Pub. Date: Aug. 3, 2023

(65) Prior Publication Data
US 2025/0349421 A1 Nov. 13, 2025

(30) Foreign Application Priority Data
Jan. 26, 2022 (CN) ........................ 202210094089.7

(51) Int. Cl.
*G16H 50/20* (2018.01)
*G06T 5/92* (2024.01)
(Continued)

(52) U.S. Cl.
CPC ............... *G16H 50/20* (2018.01); *G06T 5/92* (2024.01); *G06T 7/0012* (2013.01); *G16H 30/40* (2018.01);
(Continued)

(58) Field of Classification Search
None
See application file for complete search history.

(56) References Cited

U.S. PATENT DOCUMENTS

| | | | | |
|---|---|---|---|---|
| 2022/0012890 A1* | 1/2022 | Wu | ........................... | G06T 7/11 |
| 2022/0208355 A1* | 6/2022 | Li | ............................ | G06N 3/09 |
| 2023/0196572 A1* | 6/2023 | Nair | .......................... | G06T 7/11 351/200 |

OTHER PUBLICATIONS

Detection of diabetic retinopathy using a fusion of textural and ridgelet features of retinal images and sequential minimal optimization classifier, by Ramasamy et al., PeerJ Comput. Sci. 7:e456 DOI 10.7717/peerj-cs.456, Published May 7, 2021 (Year: 2021).*

* cited by examiner

*Primary Examiner* — Vikkram Bali
(74) *Attorney, Agent, or Firm* — Procopio, Cory, Hargreaves & Savitch LLP

(57) ABSTRACT

A depth network detection method for diabetic retinopathy based on a genetic fuzzy tree. The method includes: first, enhancing a retina image to widen a lesion area, and compress a normal area; next, building a network model U-net to accurately segment images of retinal blood vessels and blood vessel tips; subsequently, performing training according to the vascular images segmented by the model and real diagnosis results, so as to construct an interpretable
(Continued)

fuzzy decision tree; then, encoding weights of the decision tree and constructing a fitness function, and a plurality of decision trees being combined and optimized based on a genetic algorithm; and finally, introducing an accuracy index to dynamically adjust a penalty term in a loss function.

4 Claims, 4 Drawing Sheets

(51) Int. Cl.
*G06T 7/00* (2017.01)
*G16H 30/40* (2018.01)

(52) U.S. Cl.
CPC ............... *G06T 2207/20081* (2013.01); *G06T 2207/20084* (2013.01); *G06T 2207/30041* (2013.01); *G06T 2207/30096* (2013.01); *G06T 2207/30101* (2013.01)

DEPTH NETWORK DETECTION METHOD FOR DIABETIC RETINOPATHY BASED ON GENETIC FUZZY TREE

CROSS-REFERENCE TO RELATED APPLICATION

This patent application is a national stage of International Application No. PCT/CN2023/077768, filed on Feb. 23, 2023, which claims the priority of Chinese Patent Application No. 202210094089.7 filed with the China National Intellectual Property Administration on Jan. 26, 2022. Both of the aforementioned applications are incorporated by reference herein in their entireties.

TECHNICAL FIELD

The present disclosure relates to the technical field of intelligent processing of medical information, in particular to a depth network detection method for diabetic retinopathy based on a genetic fuzzy tree.

BACKGROUND

Retinal images contain information of blood vessel which is closely related to blinding diseases in ophthalmology. The health status of retinal blood vessels is of great significance for doctors to diagnose diabetic, cardiovascular and cerebrovascular diseases and various ophthalmic diseases as early as possible. However, since retinal blood vessels have complex structures and are easily influenced by the illumination factors in the collection environment, clinical manual segmentation of retinal blood vessels is not only a huge workload, but also requires high experience and skills of medical personnel. In addition, different medical personnel may have different segmentation results for the same retinal image, and manual segmentation can no longer meet the clinical demands.

With the continuous development of computer technology, the retinal vascular images in electronic medical records are automatically segmented using artificial intelligence technology so as to assist in diagnosis and decision-making of ophthalmic diseases, which has become a research focus for scholars at home and abroad. Deep learning has gained great attention in the field of image processing because of its high prediction accuracy in the identification application. A convolutional neural network model in deep learning has unique advantages in image processing because of its special structure of local perception and parameter sharing. This patent analyzes and processes retinal image data from two perspectives of deep learning and the fuzzy decision tree, and segments and predicts retinopathy images.

SUMMARY

The objective of some embodiments of the present disclosure is to solve the above problems and proposes a depth network detection method for diabetic retinopathy based on a genetic fuzzy tree.

In order to achieve the above objective, the present disclosure adopts the following technical solution.

A depth network detection method for diabetic retinopathy based on a genetic fuzzy tree includes the following steps:

S1: enhancing a retina image, where a lesion area of the retina image and a normal area around the lesion area show visually obvious different features and are formed as different image areas, and an interested lesion area of the retina image is widened and an uninterested background area of the retina image is compressed by using an image enhancement Gamma correction method;

S2, building a network model U-net, where the network model U-net is divided into a compression path and an expansion path, and includes four down-samplings and four up-samplings, two convolutions and one maximum pooling are performed prior to each sampling, the retina image is subjected to feature compression by four down-samplings in the compression path, an effective feature layer obtained by a last down-sampling is subjected to four up-samplings in the expansion path, corresponding feature layers in the down-sampling are connected, a retinal feature map is normalized by 1*1 convolution, and the built model is trained with enhanced image data to obtain an image segmentation model;

S3, fuzzing a vascular image segmented by the image segmentation model, calculating a membership degree of an attribute in the image and a fuzzy information gain, which together with a real diagnosis result are used for training to obtain a decision rule of each branch node of a fuzzy decision tree and a result set of leaf nodes for classification and prediction;

S4: encoding each node of the decision tree, constructing a fitness function to measure pros and cons of a fuzzy tree model from two aspects of accuracy and complexity, where an accurate function E indicates the accuracy of the model, and as E decreases, the accuracy increases, and a number M of the leaf nodes of the tree reflects the complexity, as M decreases, the complexity of the model decreases, and a fitness function s(T) is defined as follows:

$$s(T) = W_E \times \frac{1}{E} + W_M \times \frac{1}{M}, \quad (1)$$

where $W_E$ and $W_M$ are the weights of the accuracy E and the number M of the leaf nodes, respectively, $W_E+W_M=1$, and s(T) represents fitness of a tree T;

combining and optimizing a plurality of decision trees based on a genetic algorithm;

S5: dynamically adjusting a penalty term in a loss function according to a distance between a sample class and a true value by introducing an accuracy index, so as to further improve classification accuracy.

As the preferred technical solution of the present disclosure: the specific steps of S2 are as follows:

Step S2.1, dividing a retinopathy data set into a training set and a verification set according to a ratio of 9:1, and inputting the training set and the verification set into a training network;

Step S2.2: building a compression path of the network model U-net, and performing four down-samplings on the retina image in the compression path to obtain five preliminary effective feature layers, where each preliminary effective feature layer is a stack of convolution and maximum pooling, the retina image with an input size of 565*584 is subjected to convolution operation for twice by a 3*3 convolution kernel, edge information of the image is discarded in each convolution, 2*2 maximum pooling is performed on the retina image with a size of 561*580 obtained after the convolution operation, and each down-sampling doubles a number of channels of the retinal feature map by twice;

Step S2.3: building the expansion path of the network model U-net, where the expansion path comprises 4 up-samplings, each up-sampling reduces a number of channels of a retinal feature map in an upper layer to half by 2*2 deconvolution, a length and a width of the image are doubled, corresponding feature layers in the down-sampling are connected during up-sampling, and due to the discarding of edge information in the image during convolution, appropriate cropping is performed during connection to ensure that image sizes before and after connection are consistent, and the retinal feature map is normalized by using 1*1 convolution via the network model U-net;

Step S2.4: adopting loss function with cross entropy and SoftMax, and predicting probabilities that a class of each pixel in the retinopathy image belongs to the lesion area and the normal area to be p and 1−p, respectively, where the SoftMax function in the pixel form is:

$$p_k(x) = \frac{e^{ak(x)}}{\sum_{k=1}^{K} e^{ak(x)}}, \tag{2}$$

where ak(x) indicates an activation value of a pixel x in a k-th layer of the feature map, K is a number of classes, and $p_k(x)$ is a classification result of the pixel x by the class k;

the cross entropy loss function E is defined as:

$$E = \sum_{x\in\Omega} w(x) \times \log(p_{l(x)}(x)), \tag{3}$$

where Ω={1, . . . , K}, l(x) is a real label of each pixel x, $p_{l(x)}(x)$ is a classification result of the real label, and w(x) is a weight map of each pixel x, which distinguishes the weight of each pixel, and a calculation formula of the weight is as follows:

$$w(x) = w_c(x) + w_0 \times \exp\left(-\frac{(d_1(x) + d_2(x))^2}{2\sigma^2}\right), \tag{4}$$

where $w_c(x)$ is a weight map used to balance a certain frequency, and is ranked from near to far according to the distance from the pixel x to boundary of retinopathy, $d_1(x)$ indicates a distance ranked first, $d_2(x)$ indicates a distance ranked second, and $w_0$ is an initial value of weight, and is set to 10 and a standard deviation σ is set to 5;

Step S2.5: training and optimizing the network with a random gradient descent of a convolutional neural network framework Caffe, where the built model is trained with a goal of minimizing the loss function and maximizing the prediction accuracy.

As the preferred technical solution of the present disclosure: the specific steps of S3 are as follows:

Step S3.1, fuzzing a lesion area of a retinal blood vessel, especially the lesion edge area, to obtain a membership degree of a continuous value attribute of the image, where the fuzzed attribute value is a membership degree of an interval [0,1], which describes inaccurate information of the lesion area edge naturally and reasonably;

Step S3.2: calculating a fuzzy information gain of the attribute of the retinopathy area, where $A=\{u_i, \mu_A(u_i), u_i \in U\}$ is set as a fuzzy attribute set with a membership function $\mu_A(u_i)$ in an attribute set U, a Gaussian membership function $\mu_A(u_i)$ is calculated as in Formula 5, $U=\{u_1, u_2, \ldots, u_i, \ldots, u_m\}$ is a discrete set of attributes, m is a number of attributes, a fuzzy degree of a i-th attribute is $\mu_i=\mu_A(u_i)$, and the fuzziness measure E(A) of the fuzzy set A is:

$$\mu_A(u_i) = e^{\frac{-(u_i-c)^2}{2\sigma^2}}, \tag{5}$$

$$E(A) = -\frac{1}{m}\sum_{i=1}^{m}(\mu_i \times \ln\mu_i + (1-\mu_i)\times\ln(1-\mu_i)), \tag{6}$$

where c is a mean of normal distribution, and σ is a standard deviation of the normal distribution;

selecting the attribute with a highest fuzzy information gain as an attribute of a root node;

Step S3.3, constructing a fuzzy subclass set $A_m$ corresponding to a node according to an attribute of a parent node, a training set corresponding to the parent node, and an attribute value of the node on the attribute of the parent node, and calculating the fuzzy information gain of each fuzzy subset on the fuzzy subclass set $A_m$ according to a target class to be divided $C=\{c_1, c_2, \ldots, c_m\}$;

Step S3.4: calculating a confidence degree $B_{c_i}$ of a target class $c_i$ in a node Node, i=1, 2, 3, . . . , m, and determining whether to generate a leaf node according to a predetermined maximum confidence degree β and a predetermined minimum confidence degree α:

$$\text{Node} = \begin{cases} LeafNode, \text{ if } B_{c_i} > \beta \text{ and } B_{c_i} < \alpha \\ \max\{E(a_j)\}(a_j \in A_n), \text{ if } \alpha < B_{c_i} < \beta, \\ LeafNode, \text{ if } A_n = \phi \end{cases} \tag{7}$$

where $A_n$ is a set of unused attributes in the fuzzy subclass set $A_m$, n<m, $a_j$ is a j-th attribute in the attribute set $A_n$, ij=1, 2, . . . , n, and LeafNode represents the leaf node;

Step S3.5: constructing a child node according to an attribute values of an extended attribute of the node, and recursively processing each child node.

As the preferred technical solution of the present disclosure: the specific steps of Step S4 are as follows:

Step S4.1: encoding the fuzzy decision tree trained in the S3 and converting the fuzzy decision tree into an individual form that is capable of being solved by a genetic algorithm, where a root node number $N_0$ is set to 1, when a non-root node is a left child node, a number $N_l$ of the non-root node is $N_l=2\times N_p$, $N_p$ is a number of a parent node, and when the non-root node is a right child node, a number of the non-root node $N_r$ is $N_r=2\times N_p+1$, after each node number is obtained, a quadruple is constructed in order with a number of the node itself, a number of a left node and a number of a right child node and a number of a parent node as a code $N_{code}$ of the node, if there is no parent node or no child node, a code value at the corresponding position is 0, and codes of various nodes in the tree are connected to obtain a code matrix of the whole tree;

Step S4.2: measuring pros and cons of the fuzzy tree model from two aspects of accuracy and complexity in predicting retinopathy, where an accurate function E indicates the accuracy of the model, as E decreases, the accuracy increases, that is, the accuracy in predicting retinopathy increases, a number M of the leaf nodes of the tree reflects the complexity, as M decreases, the complexity of the model decreases, and a fitness function s(T) is:

$$s(T) = W_E \times \frac{1}{E} + W_M \times \frac{1}{M}, \tag{8}$$

where $W_E$ and $W_M$ are weights of the accuracy E and the number M of leaf nodes, respectively, $W_E+W_M=1$, and s(T) represents a fitness of the tree T;

solving, according to the constructed fitness function, the fitness of each retinopathy fuzzy tree, that is, initializing the population;

Step S4.3: selecting a pair of parent individuals according to the fitness of each fuzzy tree by a roulette method, where a probability that each fuzzy tree is selected is proportional to its fitness value, a total number of individuals is set to N, a fitness value of an individual $x_i$ is expressed as $f(x_i)$, a probability that the individual is selected is $p(x_i)$, a cumulative probability is $q(x_i)$, and the corresponding calculation formula is as follows:

$$p(x_i) = \frac{f(x_i)}{\sum_{j=1}^{N} f_j}, \tag{9}$$

$$q(x_i) = \sum_{j=1}^{i} p(x_j), \tag{10}$$

where the cumulative probability $q(x_i)$ represents a sum of selection probabilities of all individuals before an individual, which is equivalent to a range of the roulette which has been passed through, as the range increases, the selection probability of the individual increases;

Step S4.4: randomly selecting an intersection point k for the parent individual, performing an intersection operation with a probability $P_c$ to generate a new individual, and randomly generating a mutation probability $P_m$ in [0,1] for each gene of the new individual to perform mutation;

Step S4.5: recalculating a fitness of the new individual in the environment to compare with an optimal value, updating a population, and when a maximum number of evolutionary generations T=150 or a fitness of an optimal individual and a fitness of the populations do not increase for 10 consecutive generations, obtaining a generation of individuals with a highest fitness, that is, obtaining an optimal fuzzy decision tree.

The present disclosure has the following beneficial effect.

1. In the present disclosure, features of medical images are considered, a genetic fuzzy tree is fused in the deep learning network, and inaccurate information of the retinal vascular lesion area edge is described more naturally and reasonably, so that the accuracy and interpretability of model results are enhanced. Better results can be obtained when data scale is limited. The penalty terms in a loss function is dynamically adjusted according to the distance between a sample class and a true value by introducing an accuracy index, so as to further improve the classification accuracy.
2. The depth network detection method for diabetic retinopathy based on the genetic fuzzy tree according to the present disclosure can accurately segment the vascular images in the retina and identify peripheral vessels more accurately. By analyzing and classifying the extracted retinal features through the fuzzy decision tree, the detection accuracy can be improved, the interpretability of the diagnosis results can be enhanced, and the reliability of the diagnosis results can be effectively improved. The structure of the fuzzy tree is optimized by a genetic algorithm, which further improves the detection accuracy, helps doctors diagnose diabetic retinopathy effectively, and allows patients to obtain a best treatment period.

BRIEF DESCRIPTION OF THE DRAWINGS

The present disclosure will be further described with reference to the accompanying drawings.

DETAILED DESCRIPTION OF THE EMBODIMENTS

In order to make the objective, technical solution and advantages of the present disclosure more clear, the present disclosure will be further described in detail below in combination with embodiments hereinafter. Of course, the examples described with reference to the drawings are only for explaining the present disclosure, and should not be constructed as limiting the present disclosure.

Figure 1:
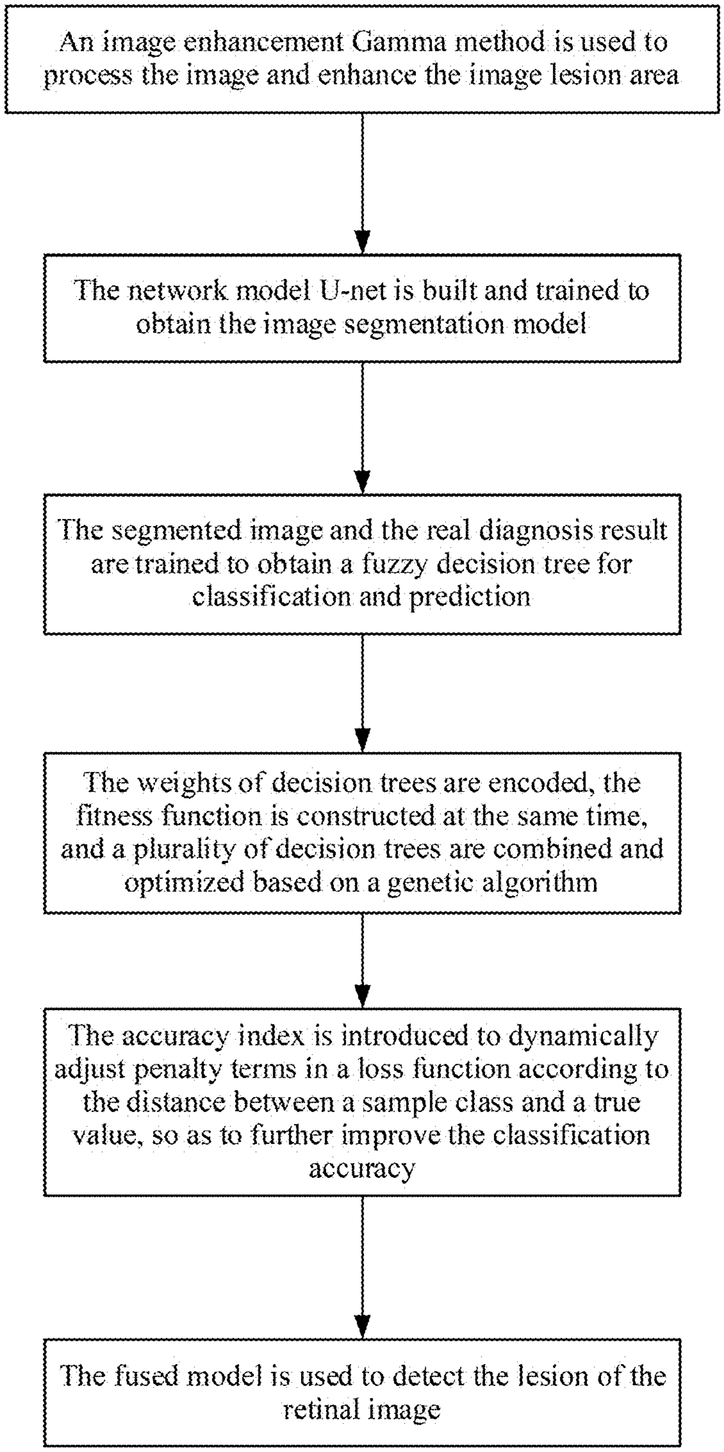
FIG. 1 is a flowchart of a depth network detection method for diabetic retinopathy based on a genetic fuzzy tree according to the present disclosure.

As shown in FIG. 1, the present disclosure discloses a depth network detection method for diabetic retinopathy based on a genetic fuzzy tree, and belongs to the field of intelligent processing of medical information. The method includes the following steps.

In S1, a retina image is enhanced. Specifically, a lesion area of the retina image and a normal area around the lesion area show visually obvious different features and are formed as different image areas, and an interested lesion area of the image is widened and an uninterested background area of the image is compressed by using an image enhancement Gamma correction method.

In S2, a network model U-net is built, the network model U-net is divided into a compression path and an expansion path and includes four down-samplings and four up-samplings, and two convolutions and one maximum pooling are performed prior to each sampling. The retina image is subjected to feature compression by four down-samplings in the compression path, an effective feature layer obtained by the last down-sampling is subjected to four up-samplings in the expansion path, the corresponding feature layers in the down-sampling are connected, finally, a retinal feature map is normalized by 1*1 convolution, and the built model is trained with the enhanced image data to obtain an image segmentation model.

In S3, a vascular image segmented by the model is fuzzed, and then a fuzzy information gain and a membership degree of attributes in the fuzzed vascular image are calculated, which together with a real diagnosis result are used for training to obtain a decision rule of branch nodes of a fuzzy decision tree and a result set of leaf nodes, for further classification and prediction.

In S4, each node of the decision tree is encoded, and a fitness function is constructed which measures pros and cons of a fuzzy tree model from two aspects of accuracy and complexity. An accurate function E is used to characterize the accuracy of the model, smaller E indicates higher accuracy, and a number M of the leaf nodes of the tree is used to reflect the complexity of the model, smaller M indicates lower complexity of the model, and the fitness function s(T) is defined as follows:

$$s(T) = W_E \times \frac{1}{E} + W_M \times \frac{1}{M}, \quad (1)$$

where $W_E$ and $W_M$ are weights of the accuracy E and the number M of leaf nodes, respectively, $W_E+W_M=1$, and s(T) represents a fitness of a tree T;

Multiple decision trees are combined and optimized based on a genetic algorithm.

In S5, a penalty term in a loss function is dynamically adjusted according to the distance between a sample class and a true value by introducing an accuracy index, so as to further improve the classification accuracy.

The specific steps of the step S2 are as follows.

In step S2.1, a retinopathy data set is divided into a training set and a verification set according to a ratio of 9:1, and the training set and the verification set are input into a training network.

In step S2.2, the compression path of the network model U-net is built, down-sampling are performed on the retina image for four times in the compression path to obtain five preliminary effective feature layers, each preliminary effective feature layer is a stack of convolution and maximum pooling. The retina image with an input size of 565*584 is subjected to convolution operation for twice by a 3*3 convolution kernel, and the edge information of the image is discarded in each convolution, 2*2 maximum pooling is performed on the retina image with a size of 561*580 obtained by convolution, and each down-sampling doubles the number of channels of the retinal feature map.

In step S2.3, the expansion path of the network model U-net is built, which comprises four up-samplings. Each up-sampling reduces the number of channels of the retinal feature map in the upper layer to half by 2*2 deconvolution, and doubles a length and a width of the image, and further, the corresponding feature layers in the down-sampling are connected during up-sampling. Since the edge information of the image is discarded during convolution, appropriate cropping is introduced during connection to ensure that the image sizes before and after connection are consistent, and the U-net network uses 1*1 convolution to normalize the retinal feature map.

In step S2.4, the loss function with cross entropy and SoftMax are adopted, and the probabilities that a class of each pixel in the retinopathy image belongs to the lesion area and the normal area are predicated to be p and 1−p, and the SoftMax function in the pixel form is:

$$p_k(x) = \frac{e^{ak(x)}}{\Sigma_{k=1}^{K} e^{ak(x)}}, \quad (2)$$

where ak(x) indicates an activation value of a pixel x in a k-th layer of the feature map, K is a number of the classes, and $p_k(x)$ is a classification result of the pixel x for the class k.

The cross entropy loss function E is defined as:

$$E = \Sigma_{x\in\Omega} w(x) \times \log(p_{l(x)}(x)) \quad (3)$$

where $\Omega=\{1, \ldots, K\}$, l(x) is a real label of each pixel x, $p_{l(x)}(x)$ is a classification result of the real label, and w(x) is a weight map of each pixel x, which distinguishes the weight of each pixel. And, a calculation formula of the weight is as follows:

$$w(x) w_c(x) + w_0 \times \exp\left(-\frac{(d_1(x)+d_2(x))^2}{2\sigma^2}\right), \quad (4)$$

where $w_c(x)$ is a weight map used to balance a certain frequency, and is ranked from near to far according to the distance from the pixel x to the boundary of retinopathy, $d_1(x)$ indicates a distance ranked first, $d_2(x)$ indicates a distance ranked second, and $w_0$ is an initial value of the weight and preferably, is set to 10, and a standard deviation σ is set to 5.

In step S2.5, the network is trained and optimized through a random gradient descent of a convolutional neural network framework Caffe, and the built model is trained with a goal of minimizing the loss function and maximizing the prediction accuracy.

The specific steps of step S3 are as follows.

In step S3.1, the lesion area of retinal blood vessels, especially the lesion edge area, is fuzzed, to obtain a membership degree of a continuous value attributes of the image, in which the fuzzed attribute value is the membership degree within an interval [0,1], which describes inaccurate information of the lesion area edge more naturally and reasonably.

In step S3.2, a fuzzy information gain of the attribute of the retinopathy area is calculated, $A=\{(u_i, \mu_A(u_i)), u_i\in U\}$ is a fuzzy attribute set with a membership function $\mu_A(u_i)$ in the attribute set U, a Gaussian membership function $\mu_A(u_i)$ is calculated as in Formula 5, $U=\{u_1, u_2, \ldots, u_i, \ldots, u_m\}$ is a discrete set of attributes, m is a number of attributes, a fuzziness of a i-th attribute is $\mu_i=\mu_A(u_i)$, the fuzziness measure E(A) of the fuzzy set A is:

$$\mu_A(u_i) = e^{\frac{-(u_i-c)^2}{2\sigma^2}}, \quad (5)$$

$$E(A) = -\frac{1}{m}\sum_{i=1}^{m}(\mu_i \times \ln\mu_i + (1-\mu_i)\times\ln(1-\mu_i)), \quad (6)$$

where c is a mean of normal distribution, and σ is a standard deviation of the normal distribution.

A attribute with a highest fuzzy information gain is selected as the attribute of a root node.

In step S3.3, a fuzzy subclass set $A_m$ corresponding to a node is constructed according to the attribute of a parent node, a training set corresponding to the parent node, and an attribute value of the node on the attribute of the parent node, and the fuzzy information gain of each fuzzy subset on the fuzzy subclass set $A_m$ is calculated according to the target class to be divided $C=\{c_1, c_2, \ldots, c_m\}$.

In step S3.4: a confidence degree $B_{c_i}$ of a target class $c_i$ in the node Node is calculated, i=1, 2, 3, . . . , m, and whether to generate a leaf node is determined according to a specified maximum confidence level β and a minimum confidence level α:

$$\text{Node} = \begin{cases} \textit{LeafNode}, \text{ if } B_{c_i} > \beta \text{ or } B_{c_i} < \alpha \\ \max\{E(a_j)\}(a_j \in A_n), \text{ if } \alpha < B_{c_i} < \beta, \\ \textit{LeafNode}, \text{ if } A_n = \varnothing \end{cases} \tag{7}$$

where $A_n$ is a set of unused attributes in the fuzzy subclass set $A_m$, n<m, $a_j$ is a j-th attribute in the attribute set $A_n$, j=1, 2, . . . , n, and LeafNode represents the leaf node.

In step S3.5: a child node is constructed according to an attribute value of an extended attribute of the node, and each child node is recursively processed.

The specific steps of the step S4 are as follows.

In step S4.1, the fuzzy decision tree trained in the step S3 is encoded, so as to be converted into an individual form that can be solved by a genetic algorithm. Specifically, the root node number $N_0$ is set to 1, and when a non-root node is a left child node, its number $N_l$ is $N_l=2\times N_p$, in which $N_p$ is a parent node number; when the non-root node is a right child node, its number $N_r$ is $N_r=2\times N_p+1$. After each node number is obtained, a quadruple is constructed in order with the number of the node itself, the number of the left node and the right child node and the number of the parent node as a code $N_{code}$ of the node. If there is no parent node or no child node, the code value at the corresponding position is 0, and the codes of each node in the tree are connected to obtain a code matrix code of the whole tree.

In step S4.2, pros and cons of the fuzzy tree model are measured from two aspects of accuracy and complexity of predicting retinopathy, an accurate function E is used to characterized the accuracy of the model, smaller E indicates higher accuracy, that is, higher accuracy of predicting retinopathy, and a number M of the leaf nodes of the tree reflects the complexity, smaller M indicates lower complexity of the model, and the fitness function s(T) is:

$$s(T) = W_E \times \frac{1}{E} + W_M \times \frac{1}{M}, \tag{8}$$

where $W_E$ and $W_M$ are a weight of accuracy E and a weight of the number M of leaf nodes, respectively, $W_E+W_M=1$, and s(T) represent the fitness of the tree T.

According to the constructed fitness function, the fitness of each retinopathy fuzzy tree is solver, that is, the population is initialized.

In step S4.3: according to the fitness of each fuzzy tree, a pair of parent individuals is selected by a roulette method, a probability that each fuzzy tree is selected is proportional to its fitness value. Assuming than a total number of individuals is N, a fitness value of an individual $x_i$ is expressed as $\mu(x_i)$, a probability that the individual is selected is $p(x_i)$, a cumulative probability is $q(x_i)$, then a corresponding calculation formula is as follows:

$$p(x_i) = \frac{f(x_i)}{\sum_{j=1}^{N} f_j}, \tag{9}$$

$$q(x_i) = \sum_{j=1}^{i} p(x_j), \tag{10}$$

where the cumulative probability $q(x_i)$ represents a sum of the selection probabilities of all individuals before an individual, which is equivalent to a range of the roulette being passed through, the larger the range is, the more likely the individual is selected.

In step S4.4, for the parent individual, an intersection point k is randomly selected, an intersection operation is performed with a probability $P_c$ to generate a new individual, and a mutation probability $P_m$ in [0,1] is randomly generated for each gene of the new individual to perform mutation.

In step S4.5, a fitness of the new individual in the environment is recalculated, to compare with an optimal value, for updating a population. And when a maximum number of evolutionary generations T=150 or a fitness of an optimal individual and a fitness of the population do not increase for 10 consecutive generations, to obtain a generation of individuals with a highest fitness, that is, an optimal fuzzy decision tree.

Figure 2:
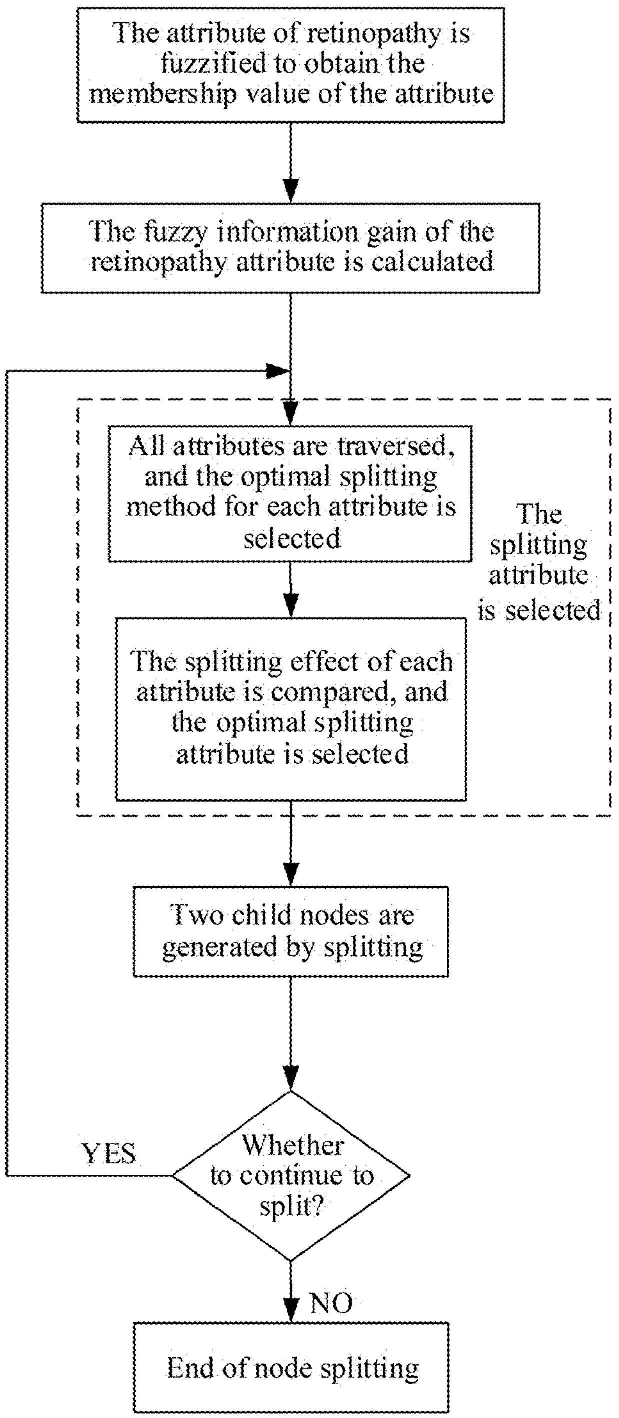
FIG. 2 is a flowchart of generating a fuzzy decision tree for predicting presence of lesion in a segmented retinal image according to the present disclosure.
Figure 3:
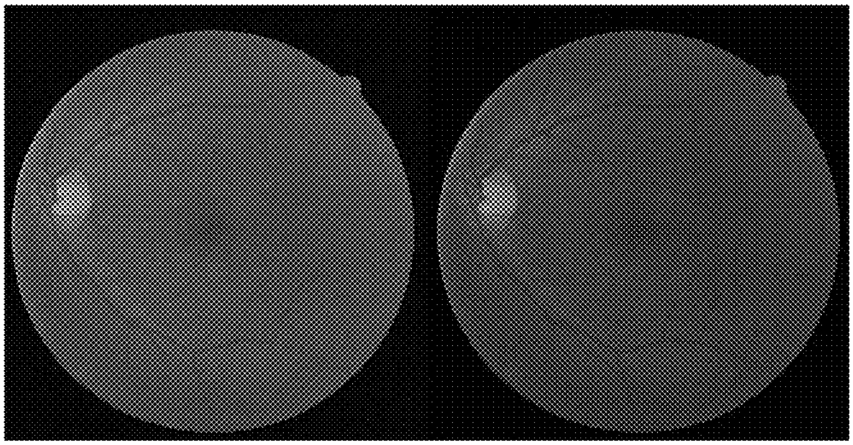
FIG. 3 is a contrast diagram of Gamma image enhancement in image preprocessing according to the present disclosure, in which a left diagram is a black-and-white diagram of an original image, and a right diagram is an enhancement effect diagram with gamma=1.2.
Figure 4:
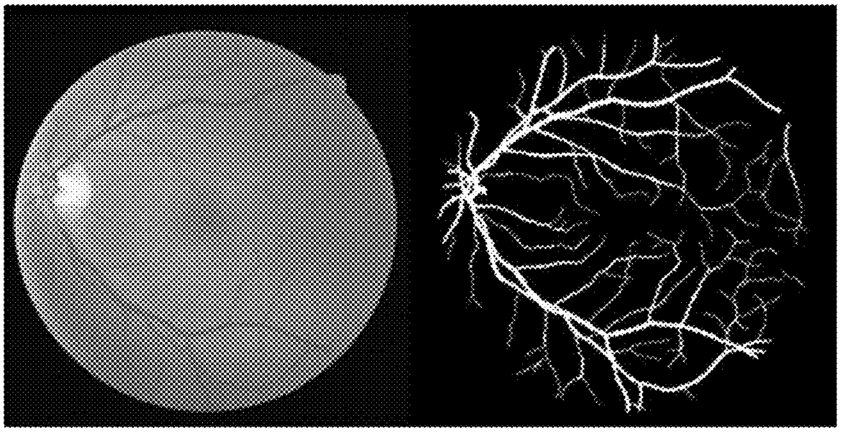
FIG. 4 is a diagram of retinal blood vessels segmented by a network model U-net according to the present disclosure, in which a left diagram is an original image, and a right diagram is a segmented image.
Figure 5:
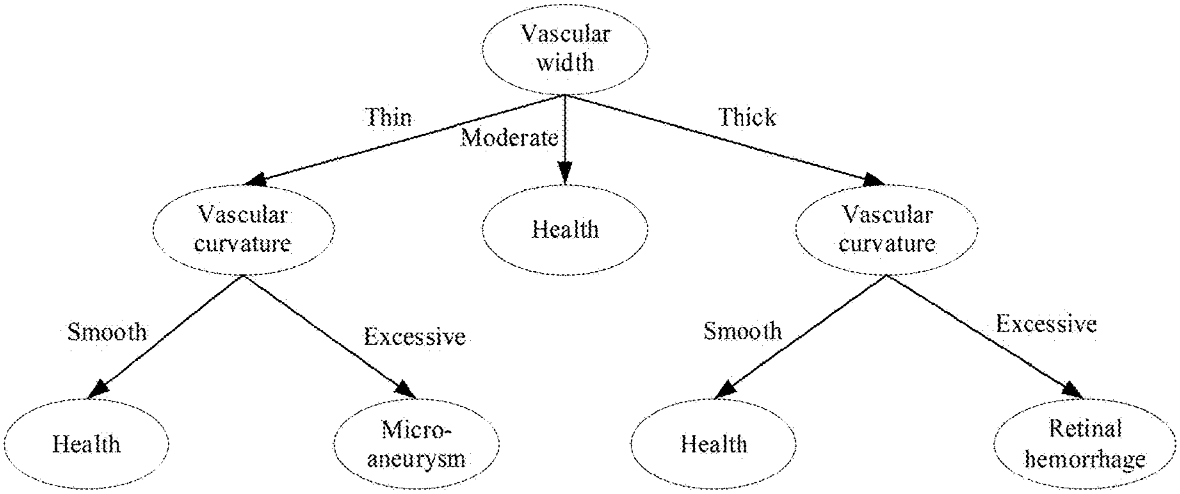
FIG. 5 shows branch segment of a built fuzzy decision tree established according to the present disclosure.
Figure 6:
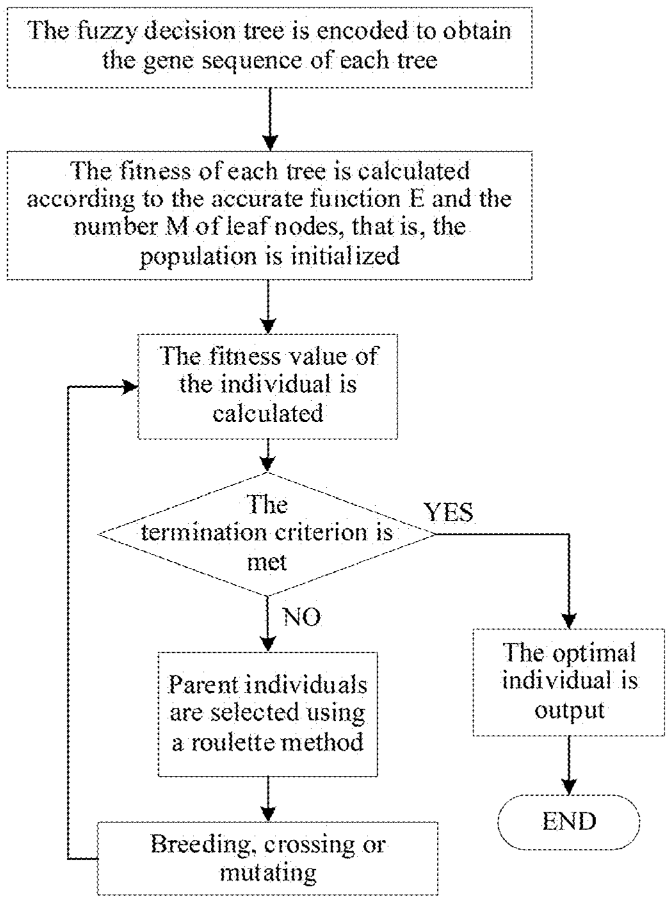
FIG. 6 is a flowchart of an optimization of the generated fuzzy decision tree by a genetic algorithm according to the present disclosure.

In the present disclosure, an image enhancement Gamma method is used to preprocess the retina image data set, as shown in FIG. 3. The left side is an original image, and the right side is an enhancement effect diagram when Gamma=1.2. The data set is then divided into a training set and a verification set according to a ratio of 9:1. The segmentation network U-net is trained, and when the loss function reaches the minimum, the segmentation result is shown in FIG. 4, in which the left diagram is an original image, the middle diagram is a label mask, and the right diagram is the segmentation result of U-net. The features of the retinal vascular image, such as vascular width, vascular curvature and fractal dimension, are selected as decision-making attributes. The fuzzy decision tree is established according to the method shown in FIG. 2, and FIG. 5 shows some branches of the fuzzy tree. Matrix encoding is performed on the generated fuzzy decision tree, and the genetic algorithm shown in FIG. 6 is used to optimize the fuzzy decision tree. Finally, the prediction accuracy is calculated, and the accuracy of the model is evaluated according to the distance between the sample class and the real value.

In the present disclosure, features of medical images are considered, a genetic fuzzy tree is fused in the deep learning network, so as to describe the inaccurate information of the retinal vascular lesion area edge more naturally and reasonably, and enhance the accuracy and interpretability of model results. Better results can be obtained when data scale is limited. An accuracy index is introduced to dynamically adjust penalty terms in a loss function according to the distance between a sample class and a true value, so as to further improve the classification accuracy.

The depth network detection method for diabetic retinopathy based on the genetic fuzzy tree according to the present disclosure can accurately segment the vascular images in the retina and identify the vascular tips more accurately. By analyzing and classifying the extracted retinal features through the fuzzy decision tree, the detection accuracy can be improved, the interpretability of the diagnosis results can be enhanced, and the reliability of the diagnosis results can be effectively improved. The structure of the fuzzy tree is optimized by a genetic algorithm, which further improves the detection accuracy, helps doctors diagnose diabetic retinopathy effectively, and allows patients to obtain a best treatment period.

The specific embodiments described above further explain the objective, technical solution and beneficial effects of the present disclosure in detail. It should be understood that the above descriptions are only specific embodiments of the present disclosure, and are not intended to limit the scope of the present disclosure. Any equivalent changes and modifications made by those skilled in the art without departing from the concept and the principle of the present disclosure shall fall within the protection scope of the present disclosure.

What is claimed is:

1. A depth network detection method for diabetic retinopathy based on a genetic fuzzy tree, comprising:

S1: enhancing a retina image, wherein a lesion area of the retina image and a normal area around the lesion area show visually obvious different features and are formed as different image areas, and an interested lesion area of the retina image is widened and an uninterested background area of the retina image is compressed by using an image enhancement Gamma correction method;

S2, building a network model U-net, wherein the network model U-net is divided into a compression path and an expansion path, and comprises four down-samplings and four up-samplings, two convolutions and one maximum pooling are performed prior to each sampling, the retina image is subjected to feature compression by four down-samplings in the compression path, an effective feature layer obtained by a last down-sampling is subjected to four up-samplings in the expansion path, corresponding feature layers in the down-sampling are connected, retinal feature map is normalized by 1*1 convolution, and the built model is trained with enhanced image data to obtain an image segmentation model;

S3, fuzzing a vascular image segmented by the image segmentation model, calculating a membership degree of an attribute in the image and a fuzzy information gain, which together with a real diagnosis result are used for training to obtain a decision rule of each branch node of a fuzzy decision tree and a result set of leaf nodes for classification and prediction;

S4: encoding each node of the decision tree, constructing a fitness function to measure pros and cons of a fuzzy tree model from two aspects of accuracy and complexity, wherein an accurate function E indicates an accuracy of the model, and as E decreases, the accuracy increases, and a number M of leaf nodes of the tree reflects a complexity of the model, as M decreases, the complexity of the model decreases, and a fitness function s(T) is defined as follows:

$$s(T) = W_E \times \frac{1}{E} + W_M \times \frac{1}{M}, \quad (1)$$

where $W_E$ and $W_M$ are weights of the accuracy E and the number M of leaf nodes, respectively, $W_E+W_M=1$, and s(T) represents a fitness of the tree T; combining and optimizing a plurality of decision trees based on a genetic algorithm;

S5: dynamically adjusting a penalty term in a loss function according to a distance between a sample class and a true value by introducing an accuracy, so as to further improve a classification accuracy.

2. The method according to claim 1, wherein the S2 comprises:

Step S2.1, dividing a retinopathy data set into a training set and a verification set according to a ratio of 9:1, and inputting the training set and the verification set into a training network;

Step S2.2: building a compression path of the network model U-net, performing four down-samplings on the retina image in the compression path to obtain five preliminary effective feature layers, wherein each preliminary effective feature layer is a stack of convolution and maximum pooling, the retina image with an input size of 565*584 is subjected to convolution operation for twice by a 3*3 convolution kernel, edge information of the image is discarded in each convolution, 2*2 maximum pooling is performed on the retina image with a size of 561*580 obtained after the convolution operation, and each down-sampling doubles a number of channels of the retinal feature map by twice;

Step S2.3: building an expansion path of the network model U-net, wherein the expansion path comprises four up-samplings, each up-sampling reduces a number of channels of a retinal feature map in an upper layer to half by 2*2 deconvolution, a length and a width of the image are doubled, corresponding feature layers in the down-sampling are connected during up-sampling, and due to the discarding of edge information in the image during convolution, appropriate cropping is performed during connection to ensure that image sizes before and after connection are consistent, and the retinal feature map is normalized by using 1*1 convolution via the network model U-net;

Step S2.4: adopting loss function with cross entropy and SoftMax, and predicting probabilities that a class of each pixel in the retinopathy image belongs to the lesion area and the normal area to be p and 1−p, respectively, wherein the SoftMax function in the pixel form is:

$$p_k(x) = \frac{e^{ak(x)}}{\Sigma_{k=1}^{K} e^{ak(x)}}, \quad (2)$$

where ak(x) indicates an activation value of a pixel x in a k-th layer of the feature map, K is a number of classes, and $p_k(x)$ is a classification result of the pixel x for a class k;

the cross entropy loss function E is defined as:

$$E = \Sigma_{x \in \Omega} w(x) \times \log(p_{l(x)}(x)), \quad (3)$$

where Ω={1, . . . , K}, l(x) is a real label of each pixel x, $p_{l(x)}(x)$ is a classification result of the real label, and w(x) is a weight map of each pixel x, which distinguishes the weight of each pixel, and a calculation formula of the weight is as follows:

$$w(x) w_c(x) + w_0 \times \exp\left(-\frac{(d_1(x) + d_2(x))^2}{2\sigma^2}\right), \quad (4)$$

where $w_c(x)$ is a weight map used to balance a certain frequency, and is ranked from near to far according to a distance from the pixel x to boundary of retinopathy, $d_1(x)$ indicates a distance ranked first, $d_2(x)$ indicates a distance ranked second, and $w_0$ is an initial value of the weight, and is set to 10 and a standard deviation $\sigma$ is set to 5;

Step S2.5: training and optimizing the network with a random gradient descent of a convolutional neural network framework Caffe, wherein the built model is trained with a goal of minimizing the loss function and maximizing the prediction accuracy.

3. The method according to claim 1, wherein the S3 comprises:

S3.1, fuzzing a lesion area of a retinal blood vessel, especially the lesion edge area, to obtain a membership degree of a continuous value attribute of the image, wherein the fuzzed attribute value is a membership degree within an interval [0,1], which describes inaccurate information of the lesion area edge naturally and reasonably;

Step S3.2: calculating a fuzzy information gain of the attribute of the retinopathy area, wherein $A=\{(u_i, \mu_A(u_i)), u_i \in U\}$ is set as a fuzzy attribute set with a membership function $\mu_A(u_i)$ in an attribute set U, a Gaussian membership function $\mu_A(u_i)$ is calculated as in Formula 5, $U=\{u_1, u_2, \ldots, u_i, \ldots, u_m\}$ is a discrete set of attributes, m is a number of attributes, and a fuzzy degree of a i-th attribute is $\mu_i=\mu_A(u_i)$, and a fuzziness measure E(A) of the fuzzy set A is:

$$\mu_A(u_i) = e^{\frac{-(u_i-c)^2}{2\sigma^2}}, \tag{5}$$

$$E(A) = -\frac{1}{m}\sum_{i=1}^{m}(\mu_i \times \ln\mu_i + (1-\mu_i)\times\ln(1-\mu_i)), \tag{6}$$

where c is a mean of normal distribution, and $\sigma$ is a standard deviation of the normal distribution;

selecting an attribute with a highest fuzzy information gain as an attribute of a root node;

S3.3, constructing a fuzzy subclass set $A_m$ corresponding to a node according to an attribute of a parent node, a training set corresponding to the parent node, and an attribute value of the node on the attribute of the parent node, and calculating the fuzzy information gain of each fuzzy subset on the fuzzy subclass set $A_m$ according to a target class to be divided $C=\{c_1, c_2, \ldots, c_m\}$;

Step S3.4: calculating a confidence degree $B_{c_i}$ of a target class $c_i$ in a node Node, i=1, 2, 3, . . . , m, and determining whether to generate a leaf node according to a predetermined maximum confidence degree $\beta$ and a predetermined minimum confidence degree $\alpha$:

$$\text{Node} = \begin{cases} \textit{LeafNode}, \text{ if } B_{c_i} > \beta \text{ or } B_{c_i} < \alpha \\ \max\{E(a_j)\}(a_j \in A_n), \text{ if } \alpha < B_{c_i} < \beta, \\ \textit{LeafNode}, \text{ if } A_n = \varnothing \end{cases} \tag{7}$$

where $A_n$ is a set of unused attributes in the fuzzy subclass set $A_m$, n<m, $a_j$ is a j-th attribute in the attribute set $A_n$, j=1, 2, . . . , n, and Leaf Node represents the leaf node;

Step S3.5: constructing a child node according to an attribute value of an extended attribute of the node, and recursively processing each child node.

4. The method according to claim 1, wherein the S4 comprises:

Step S4.1: encoding the fuzzy decision tree trained in the S3 and converting the fuzzy decision tree into an individual form that is capable of being solved by a genetic algorithm, where a root node number $N_0$ is set to 1, when a non-root node is a left child node, a number $N_l$ of the non-root node is $N_l=2\times N_p$, $N_p$ is a number of a parent node, and when the non-root node is a right child node, a number of the non-root node $N_r$ is $N_r=2\times N_p+1$, after each node number is obtained, a quadruple is constructed in order with a number of the node itself, a number of a left node, a number of a right child node and a number of a parent node as a code $N_{code}$ of the node, if there is no parent node or no child node, a code value at the corresponding position is 0, and codes of various nodes in the tree are connected to obtain a code matrix of the whole tree;

Step S4.2: measuring pros and cons of the fuzzy tree model from two aspects of accuracy and complexity in predicting retinopathy, where an accurate function E indicates the accuracy of the model, as E decreases, the accuracy increases, the accuracy in predicting retinopathy increases, a number M of the leaf nodes of the tree reflects the complexity, as M decreases, the complexity of the model decreases, and a fitness function s(T) is:

$$s(T) = W_E \times \frac{1}{E} + W_M \times \frac{1}{M}, \tag{8}$$

where $W_E$ and $W_M$ are weights of the accuracy E and the number M of leaf nodes, respectively, $W_E+W_M=1$, and s(T) represents a fitness of the tree T;

solving, according to the constructed fitness function, the fitness of each retinopathy fuzzy tree, that is, initializing the population;

Step S4.3: selecting a pair of parent individuals according to the fitness of each fuzzy tree by a roulette method, where a probability that each fuzzy tree is selected is proportional to its fitness value, a total number of individuals is set to N, a fitness value of an individual $x_i$ is expressed as $f(x_i)$, a probability that the individual is selected is $p(x_i)$, a cumulative probability is $q(x_i)$, and the corresponding calculation formula is as follows:

$$p(x_i) = \frac{f(x_i)}{\Sigma_{j=1}^{N} f_j}, \tag{9}$$

$$q(x_i) = \Sigma_{j=1}^{i} p(x_j), \tag{10}$$

where the cumulative probability $q(x_i)$ represents a sum of selection probabilities of all individuals before an individual, which is equivalent to a range of the roulette which has been passed through, as the range increases, the selection probability of the individual increases;

Step S4.4: randomly selecting an intersection point k for the parent individual, performing an intersection operation with a probability $P_c$ to generate a new individual, and randomly generating a mutation probability $P_m$ in [0,1] for each gene of the new individual to perform mutation;

Step S4.5: recalculating a fitness of the new individual in the environment to compare with an optimal value, updating a population, and when a maximum number of evolutionary generations T=150 or a fitness of an optimal individual and a fitness of the population do not increase for 10 consecutive generations, obtaining a generation of individuals with a highest fitness, that is, obtaining an optimal fuzzy decision tree.

* * * * *